US005258172A

United States Patent [19]

Rubin

[11] Patent Number: 5,258,172

[45] Date of Patent: Nov. 2, 1993

[54] IODINATED ALIPHATIC EMULSIONS FOR X-RAY CONTRAST

[76] Inventor: Daniel L. Rubin, 575 S. Rengstorff Ave., No. 128, Mountain View, Calif. 94004

[21] Appl. No.: 568,251

[22] Filed: Aug. 15, 1990

Related U.S. Application Data

[63] Continuation-in-part of Ser. No. 298,772, Jan. 17, 1989, abandoned, which is a continuation of Ser. No. 566,494, Dec. 29, 1983, abandoned.

[51] Int. Cl.[5] .................. G01N 23/04; A61K 31/235; C07C 69/76

[52] U.S. Cl. ....................................... 424/5; 514/543; 514/938; 560/103

[58] Field of Search ........................... 424/5; 560/103; 514/938, 543

[56] References Cited

U.S. PATENT DOCUMENTS 2,348,231 5/1944 Strain et al. .

OTHER PUBLICATIONS

Pirkey et al. Radiology 55:89–92 (1950).
Teplick et al. Radiology 82:478–485 (1964).

*Primary Examiner*—Allen J. Robinson
*Assistant Examiner*—Gary E. Hollinden

[57] ABSTRACT

Contrast agents comprising stable aqueous emulsions of iophendylate and their use in radiological examination of the small and large intestine after oral administration are described.

13 Claims, 23 Drawing Sheets

IODINATED ALIPHATIC EMULSIONS FOR X-RAY CONTRAST

CROSS REFERENCE TO RELATED APPLICATIONS

This application is a continuation-in-part of application Ser. No. 07/298,772, filed Jan. 17, 1989, now abandoned, which is a continuation of application Ser. No. 06/566,494, filed Dec. 29, 1983, now abandoned, the disclosures of which are incorporated by reference.

FIELD OF THE INVENTION

This invention relates to contrast agents and processes for their use in diagnostic radiology. More specifically, it relates to contrast agents and their use in the gastro-intestinal tract.

BACKGROUND

The use of roentgenographic (x-ray) techniques to assist in the diagnosis of medical problems is well known and long established. For example, the diagnosis of fractures, arthritic conditions and other problems associated with the skeletal system is a routine and highly effective practice. Chest x-rays to provide early detection or confirmation of lung and heart disease are also routinely done.

The use of x-rays for the purpose of visualizing these organs is facilitated because there are sufficient differences in the densities of air, bone and soft tissue to produce an image on the x-ray film. However, the performance of an x-ray on abdominal organs can be impractical, if not impossible, because the densities of these organs are so similar that a satisfactory image cannot be obtained.

Notwithstanding the fact that an organ may not be visualized on x-ray, in many instances radiological techniques of diagnosis can still be accomplished through the use of contrast agents. Ideally, such an agent, which contains a substance denser than the adjacent tissues is administered to the patient in a manner which causes the agent to be distributed throughout the organ of interest.

Among the organs commonly examined by x-ray using contrast agents is the gastro-intestinal (GI) tract. The most widely used contrast agent for the GI tract, but by no means an ideal one, is barium sulfate administered orally or rectally as a suspension. The suspensions, however have limited stability even with stabilizers, have poor palatability and are constipating. Furthermore, in the upper GI tract, the suspensions lack homogeneity, becoming flocculent under the influence of gastrointestinal secretions, and do not adhere well to mucus membranes. Barium sulfate is also highly radio-opaque to x-ray and, as a result, a segment of small bowel or colon underlying another segment is obscured because of inadequate penetration by the x-ray radiation. When given orally, barium sulfate preparations are useless as an aid in examination of the colon as no coating of the mucosa occurs, the barium sulfate forming irregular clumps with fecal material. Furthermore, when administered as an enema, barium sulfate suspensions in the presence of fecal material show the same tendencies to flocculate and to coat the mucosa poorly.

Aqueous solutions of suitable radio-opaque molecules have been proposed as contrast agents for use in the GI tract and are less constipating than barium sulfate preparations. However, they are even less palatable than barium preparations and have other substantial deficiencies which have prevented them from gaining acceptance for that purpose. For example, they are hypertonic and highly irritating to the GI tract and are even considered to be hazardous to patients in the pediatric age group. They are also poor contrast agents in the GI tract, exhibiting relatively low radio-density which is made worse by osmotic dilution. The solutions, being water soluble, produce little or no mucosal coating as well.

Another class of contrast agents used for x-ray studies are oily organic substances containing iodine to confer radio-opacity. Among these may be mentioned Ethiodol (the iodine addition product of a mixture of ethyl esters of oleic, linoleic and linolenic acids obtained from poppyseed oil), Lipiodol (the iodine addition product of glyceryl esters of oleic, linoleic and linolenic acids), Angiopaque (ethyliodosterate), the isobutyl ester of diiodobehenolic acid and iodohexadecane. It will be recognized that these agents, but for iodohexadecane, are the product of adding iodine to the olefinic sites of esters of long chain (18–22 carbon atoms) unsaturated fatty acids. These substances have found no application in the GI tract because, being oily, they are not miscible with aqueous GI contents and do not coat the mucosa.

Emulsions of this class of contrast agents have been proposed for use in the GI tract, but pose substantial problems of toxicity. Teplich used emulsions of Ethiodol. See Teplich et al., Radiology, 82, 478 (1964). Reportedly, emulsions in which the particle size had been reduced to less than 0.3 micron gave good contrast visualization in the small intestine of dogs used as test subjects. In those tests, however, 50–70% of the oil was absorbed from the GI tract of the animals. Between 20–57% of the oil was eliminated by kidney function but the balance was stored in the body, posing the threat of a toxic reaction. Teplich et al. performed some clinical trials with human test subjects without reporting any data, but the results were such that the authors concluded that "an emulsion of a completely non-absorbable" radio-opaque substance "might" be ideal for use in the GI tract. On the other hand, the result of emulsifying an oil to improve its performance as a contrast agent also reduces its particle size which increases its absorbability and potential toxicity. In any case, emulsions of Ethiodol have not gained acceptance for use in the GI tract notwithstanding the well known shortcomings of barium sulfate preparations.

The use of an aqueous emulsion comprising 50% by volume of iophendylate "sparingly in the examination of the upper gastrointestinal tract" has been reported to produce results no better than that achieved using conventional materials. See Pirkey et al., Radiology, 55, 89, 92 (1950).

From the foregoing, it will be apparent that there has gone unfilled a long felt need for a method of radiological examination of the GI tract which employs a contrast agent that is convenient to use without inflicting discomfort on the patient or posing substantial toxicity problems and which coats the mucosa well, is stable in the GI tract and, at the same time, exhibits satisfactory radio-opacity and permits transradiation to permit visualization of underlying bowel segments.

SUMMARY OF THE INVENTION

The present invention provides a greatly improved method for the radiological examination of the GI tract comprising the administration, either orally or rectally, of a contrast agent which comprises a stable aqueous emulsion of an iodinated compound selected from an aliphatic carboxylic acid or a compound convertible, at least in part, in the GI tract to the aliphatic carboxylic acid such as an ester, amide or anhydride, the carboxylic acid having an aliphatic chain, including the carboxyl group, of from 6 to 17 carbon atoms and being but slightly soluble in water.

The mixtures or emulsions of the invention may be administered orally to a patient for radiological examination of the GI tract and x-rays taken as the preparation proceeds through the esophagus, stomach, small intestine and, significantly, the colon (large intestine), an organ which has heretofore been examined only using rectally administered agents. The emulsions of the invention may also be administered rectally to a patient for radiologic examination of the colon if desired.

Accordingly, it is an object of the present invention to provide an improved method for radiological examination of the GI tract.

Another object of the invention is to achieve improved contrast visualization of the GI tract.

Yet another object of the invention is to provide improved contrast agents for oral or rectal administration for visualization of the GI tract.

A more specific object is to visualize the colon by means of orally administered contrast agents.

The manner in which these and other objects are achieved will be apparent from a consideration of the accompanying figures and the following detailed description of the invention.

DETAILED DESCRIPTION OF THE INVENTION

Figure 1:
FIGS. 1 to 8 are x-rays taken of the GI tract of a dog after oral administration of contrast agents according to the method of the present invention.
Figure 1:
Figure 1:

As already indicated, the present invention provides an improved method for the radiological examination of the GI tract comprising, as a first step, the oral administration of a contrast agent in the form of a stable aqueous emulsion of an iodinated compound selected from aliphatic carboxylic acids or compounds convertible, at least in part, in the GI tract to the aliphatic carboxylic acid, the carboxylic acid having an aliphatic chain, including the carboxylic group, of from 6 to 17 carbon atoms, not including branching, and being only slightly soluble in water. As used herein, the term "slightly soluble" means that the solubility of the iodinated compound is greater than that of Ethiodol but which is not miscible with water in all proportions. A good indication that the iodinated compound has the requisite minimum solubility is its ability to form a stable emulsion, as hereinafter defined, by simple mixing and shaking with the emulsifiers of the present invention. By contrast, it is necessary to use stringent emulsification means including high speed stirring to form stable emulsions from insoluble compounds such as Ethiodol. Preferably, the solubility of the iodinated compound in water is not greater than about 10% by volume. As further used herein, the term "stable" as applied to emulsions means that the emulsion shows no visible evidence of separation of the oil and water phases over the period after oral or rectal administration during which a radiographic examination of the upper or lower GI occurs, i.e., about 1 hour. Preferred emulsions are stable for even longer periods, i.e., at least about 12 hours and, more preferably, at least about 24 hours or longer. After either oral or rectal administration of the contrast agent, x-rays are taken at suitable time intervals as the agent passes through the GI tract. Among compounds convertible to the aliphatic acid may be mentioned amides, esters and anhydrides of the aliphatic carboxylic acid.

I have found that good contrast visualization of the GI tract can be obtained using stable emulsions according to the present invention, particularly of the small intestine and even of the large intestine (colon) by the oral route and of the colon after rectal administration. While I do not wish to be bound by any particular theory, it appears that the improved results obtained by my invention compared to prior art suspensions of barium sulfate and emulsions of Ethiodol, both of which are substantially insoluble in water, and compared to soluble contrast agents in the form of aqueous solutions are, at least in part, the result of the partial or sliqht water solubility of the iodinated compounds of the invention. Their slight water solubility permits diffusion of the iodinated compounds into the aqueous phase of the intestinal mucus and secretions which coat the mucosa without the need to form emulsions of very small particle size as is necessary with less polar, more hydrophobic and insoluble substances such as Ethiodol which coat well only when finely dispersed. Their low solubility also prevents their osmotic dilution as occurs with soluble contrast agents without substantially impairing their ability to coat the mucosa. Because larger particle sizes can be used, the absorption of the iodinated compound is reduced which reduces the possibility of toxic effects being observed.

It also appears that the aliphatic carboxylic acid structure of the iodinated compounds of the invention facilitates their packaging into bile salt micelles in the intestine which aid their transport into the mucus layer. It further appears that these iodinated compounds exhibit an affinity for the mucus and intestinal epithelium since, as will be demonstrated hereinafter, the iodinated compound persists in the mucus of the colon for up to 72 hours after oral administration and even after evacuation of all colonic content. This property is not exhibited by any contrast agent used heretofore in the GI tract.

Aliphatic iodinated compounds used in the contrast agent can be obtained by the addition of iodine to unsaturated bonds on the aliphatic chain by conventional techniques. Iodine can also be incorporated by attaching a iodinated aromatic side chain to the molecule. The latter compounds are preferred because the iodine, being bound to an aromatic group, is not physiologically labile during metabolism and is excreted with the aromatic portion of the molecule, further reducing the possible toxic side effects. Aliphatically bound iodine, on the other hand, can be released by deiodination and result in a toxic reaction.

Presently preferred iodinated compounds are aliphatic carboxylic acids, or compounds convertible, at least in part, to carboxylic acids in the GI tract having 6-17 carbon atoms in the aliphatic chain, not including branching, including the carboxyl group, and having an iodinated aromatic substituent on the chain. Such compounds and the method of their preparation are described in U.S. Pat. No. 2,348,231, the disclosure of which is incorporated herein by reference. A particularly preferred iodinated compound in this class is iophendlyate, a mixture of a major portion of ethyl 10-(p-iodophenyl)undecylate with a minor portion of ethyl 11-(p-iodophenyl)undecylate.

Generally, the class of preferred compounds is that having the formula $(I)_nX—R—C(O), R'$ wherein R is an aliphatic chain of from 5 to 16 carbon atoms, X is an aromatic group, n is an integer of from 1-3 per aromatic nucleus and R' is hydrogen, a halogen such as chlorine, fluorine or the residue of an alcohol, amine or carboxylic acid used to form an ester, amide or anhydride. While a variety of alcohols can be used to make the ester, alcohols such as ethyl and glyceryl are preferred since, if liberated in the GI tract by a saponification process, they are relatively benign substances which the body tolerates well. Preferably X is a phenyl group.

In presently preferred compositions, the amount of iodinated compound does not exceed about 45% by volume of the emulsion. The emulsifying agent can be selected from commercially available agents. Some, however, are to be preferred over others and the most satisfactory ones can be selected by simply screening available emulsifiers. For example, pectin seems to inhibit gastric emptying and is undesirable for that reason. Others form emulsions which lack sufficient stability in the GI tract for optimum results. Among these may be mentioned Myrj 45, gelatin and mixtures of Myrj 45 and Tween 20. A presently preferred emulsifier is Dow Corning Medical Antifoam AF, a composition of 30% polydimethylsiloxane and silica aerogel, 14% stearate emulsifiers, and 0.075% sorbic acid, the balance being water. Intralipid, a commercially available emulsion of fatty acids useful for parenteral nutrition, is also an effective emulsifier when used in conjunction with a suspending agent.

Other preferred formulations are emulsions prepared with suspending agents such as "Cologel", a solution of 9 gm methylcellulase per 100 cc $H_2O$ containing 5% alcohol. Also useful with the emulsions are stabilizers including, but not limited to, biopolymers such as Emulsan (Petroferm USA), a lipoheterpolysaccharide comprising a backbone of D galactosamine and aminouronic acid having fatty acid and fatty ester side chains of length ranging from $C_{10}$ to $C_{18}$, the polymers being completely N-acylated and partially O-acylated.

The emulsion may be administered orally and x-rays taken at the desired intervals of the esophagus, stomach, small intestine and the colon. The emulsion may also be administered rectally for visualization of the colon only. If radiological examination of the stomach is desired, a buffering agent should be given first to neutralize stomach acid as better coating is obtained in a non-acidic medium.

The following stable emulsions of iophenydylate (Pantopaque) have been found to provide particularly satisfactory results in the method of the invention using oral administration.

1. 36 ml Pantopaque
   120 ml water
   50 ml Dow Corning Medical Antifoam AF
   (Stable 6 hours)
2. 150 ml Pantopaque
   50 ml water
   150 ml Dow Corning Medical Antifoam AF
   (Stable >24 hours)
3. 108 ml Pantopaque
   83 ml water
   25 ml Cologel
   20 ml Intralipid
   (Stable 1-3 days)

All of the formulations were prepared by mixing the ingredients in a cup and shaking the mixture for 1 minute before oral administration. In all cases of formulations 1, 2 and 3, stable emulsions were formed.

Each of formulations 1 and 2 were orally administered on different occasions to the same dog (approximate weight, 20 kilograms) and x-rays taken of the GI tract with the dog in the right lateral position. Formulation 3 was administered to a different dog. The x-rays were taken from a distance of 40 inches to the film plane, at 100 kilovolts and 30 milliamperes seconds (300 milliamps, 0.1 sc.). Prior to administration of the contrast agent formulation, the dog was anaesthetized using 20% Surital in water. The initial does of anaesthetic was 5 cc. administered intravenously. At this level the dog maintained blink reflex but tolerated a stomach tube through which the contrast agent was admitted to the stomach. Anaesthesia was maintained by the periodic administration of ½ cc. of the Surital solution.

Figure 2:
Figure 3:

FIGS. 1, 2 and 3, respectively, are x-rays taken after administration of formulation 1, at 30 minutes, 24 hours, and 48 hours.

Figure 4:
Figure 5:

FIGS. 4 and 5, respectively, are x-rays taken after administration of formulation 2 at 30 minutes and 45 minutes.

Figure 6:
Figure 7:
Figure 8:

FIGS. 6, 7 and 8, respectively, are x-rays taken after administration of formulation 3 at 15 minutes, 30 minutes and 6 hours.

Figure 9:
FIGS. 9 and 10 are x-rays taken of the GI tract of the same animal after oral administration of a barium sulfate suspension for comparison with the method of the present invention.
Figure 10:

FIGS. 9 and 10, respectively, are x-rays taken after administration of an aqueous suspension comprising 40% by weight of barium sulfate at 30 minutes and 24 hours for the purpose of comparison with the present invention.

The advantages of the present invention over radiological examination of the GI tract using conventional barium sulfate suspensions is clear from a consideration of FIGS. 1-10. Thus, using the emulsions of formulations 1 and 2, excellent contrast visualization of the small intestine with homogeneous opacity in the lumen is obtained which is not affected by intestinal secretions. (FIGS. 1, 4 and 5). Furthermore, excellent mucosal coating is observed and overlapping intestinal loops show an excellent transradiation effect which permits visualization of each loop. (FIGS. 1, 4 and 5). In FIG. 5, it can be seen that excellent air contrast visualization of the small bowel is obtained with a thick and homogeneous layering of contrast medium on the mucosal surface.

In FIG. 4, it can further be seen that the emulsion produces a coating of the gastric mucosa.

After 24 hours from ingestion, the emulsion of iophendylate formulation 1 shows persistence of mucosal coating and contrast visualization in the terminal ileum and colon, (FIG. 2). Partial contrast visualization is retained even after 48 hours (FIG. 3). Although not shown, some persistence of coating has been observed even after 72 hours.

Similar excellent results were observed with formulation 3. After 15 minutes from ingestion (FIG. 6) uniform coating of the mucosa and excellent air contrast (see arrows) are observed and there is no evidence of phase separation. After 30 minutes from ingestion (FIG. 7), mucosal coating remains excellent and the air contrast effect is even more pronounced (see arrow). No formation of oil droplets or other evidence of phase separation is observed. In both FIGS. 6 and 7, very good visualization of overlapping loops is obtained.

After six hours from ingestion (FIG. 8) there is persistence of contrast in the small bowel (open arrow). Furthermore, contrast of the colon is now observed with excellent mucosal coating and air contrast effect (closed arrows) without evidence of oil droplet formation, column fragmentation or other evidence of phase separation.

By contrast, x-rays taken after administration of barium sulfate are substantially inferior to those obtained with the stable emulsions of iophendylate. They do not demonstrate the occurrence of transradiation through overlapping loops (FIG. 9) and no contrast visualization of the colon is obtained since the barium sulfate has formed irregular clumps with the fecal material (FIG. 10).

No substantial adverse effects on the test subject were observed after oral administration of the stable emulsions of iophendylate. Occasionally diarrhea was observed and mild lethargy persisted for up to 48 hours. No other adverse effects were noted and at least some of the effects noted may have been caused by the anaesthetic.

Figure 11:
FIG. 11 is an x-ray taken of the colon of a dog after administration by enema of a contrast agent according to the method of the present invention.
Figure 12:
FIGS. 12–17 are x-rays taken of the GI tract of a dog using a composition believed to have been known to the prior art.
Figure 13:
Figure 14:
Figure 15:
Figure 16:
Figure 17:

A stable emulsion of a formulation of Pantopaque (72 ml), water (250 ml) and Dow Corning Medical Antifoam AF (100 ml) was prepared in the manner described for the orally administered emulsions and administered to a dog by enema to evaluate the colon. A view (FIG. 11) was taken 10 minutes after administration. It shows excellent mucosal coating and air contrast effects (see arrows).

Although standard x-rays were obtained using the formulations described above, fluoroscopy or cineradiography techniques can be used as well.

As noted above, Pirkey et al., in Radiology, 55, 89 (1950) report use of an aqueous emulsion comprising 50% by volume of Pantopaque "sparingly" for upper GI tract examination with no better results than with conventional materials. They reference having used a formulation described by Chalecke et al., Radiology, 49, 131 (1947). That composition consisted of Pantopaque, water and about 1% of Igepon T as a surface active agent. Pirkey et al. did not reproduce or even describe the x-rays taken which were the basis for their conclusions. An emulsion was prepared according to the Chalecke formula and by Pirkey et al. from Pantopaque (72 ml), water (72 ml) and Igepon T gel (0.6 gm). The resulting emulsion was not stable as it showed signs of phase separation after only 15 minutes and complete phase separation occurred between 1-2 hours.

FIGS. 12-17 are radiographs of the GI tract of a dog taken 10, 15, 25, 35, 45, and 55 minutes, respectively, after administration of a freshly prepared emulsion according to the Chalecke formula used by Pirkey et al.

The radiographs taken after 10 and 15 minutes, when about ⅔ of the small intestine can be visualized, are substantially as described by Pirkey. The x-rays taken after 25, 35, 45 and 55 minutes to visualize the entire small intestine show, however, very poor visualization (see arrow in FIG. 15) as the emulsion has begun to breakdown (see droplets at arrow in FIG. 16), apparently because of concentration effects. Furthermore, the emulsion is apparently quite toxic to the animal since it was still lethargic for a full 24 hours after administration.

Figure 18:
FIGS. 18 is an x-ray taken of the colon of a dog after administration by enema of a composition believed to have been known to the prior art.

The same Chalecke formulation was administered to a dog by way of enema for colon evaluation. A view (FIG. 18) was taken 10 minutes after administration. From this view it is clear that fragmentation, phase separation and poor mucosal coating has occurred. There are multiple air-filled segments of the colon that exhibit no mucosal coating at all (see arrows).

Figure 19:
FIGS. 19, 20, and 21 are x-rays taken of the GI tract of a dog after oral administration of an unstable emulsion of Pantopaque.
Figure 20:
Figure 21:

A second unstable emulsion was prepared from Pantopaque (108 ml), water (108 ml) and Medical Antifoam AF (0.8 ml). This emulsion showed visible phase separation in 15 minutes and separation was complete within 30 minutes. FIGS. 19, 20, and 21 are x-rays taken after 15 minutes, 30 minutes, and 24 hours respectively after administration to a dog. FIGS. 19 and 20 demonstrate graphically the effect of using an unstable emulsion as fragmentation of the contrast column (arrows in FIG. 19) and phase separation (arrows in FIG. 20) have occurred. There are also bowel segments which lack any coating (arrows in FIG. 19). This condition is unchanged after 30 minutes (FIG. 20). After 24 hours (FIG. 21), the contrast column has entered the colon but coating is not uniform, thin in some areas and undesirably thick in others.

These results with the unstable emulsion used by Pirkey et al. and that described above stand in marked contrast to those observed in connection with the stable formulations used to obtain FIGS. 1-8 and 11 which are described above. For example, FIG. 5 shows excellent mucosal coating and contrast visualization of the small intestine 45 minutes after oral administration, with no sign of emulsion breakdown. FIG. 2 shows excellent coating of the colon after 24 hours of administration. Furthermore, in those cases the test animals recovered rapidly from the treatment regimen.

Figure 22:
FIGS. 22 and 23 are x-rays taken of a dog using an unstable emulsion of Ethiodol.
Figure 22:
Figure 23:

An emulsion was prepared using the same formulation as described by Pirkey et al. except that Ethiodol was substituted for Pantopaque. A second emulsion of Ethiodol (30 ml), water (150 ml) and Dow Corning Medical Antifoam AF (30 ml) was also prepared. Neither emulsion was stable (substantial phase separation within 30 minutes of emulsification). The second of these emulsions was administered orally to a dog and x-rays taken after 15 minutes (FIG. 22) and 30 minutes (FIG. 23). Consideration of those views demonstrate that administration of the unstable emulsion led to fragmentation of the column of radiopaque, contrast agent droplet formation (see curved arrows) resulting from emulsion phase separation, and poor coating of the mucosa (see straight arrows).

These results further confirm that, to obtain stable emulsions of the insoluble Ethiodol as described by Teplich, it is necessary to use more stringent emulsification means in order to obtain Ethoidol particles which are sub-micron in size. Such small particles, however, pose a substantial risk of toxicity to the patient.

From the foregoing, it will be apparent that the present invention provides a greatly improved method for radiologic examination of the GI tract compared to accepted prior art practices. Unexpectedly, even satisfactory visualization of the colon can be obtained by oral administration of a contrast agent of this invention eliminating, in many cases at least, the need for cleansing the colon using a laxative or enema. Furthermore, the procedure is simpler than conventional methods for visualizing the colon which require extremely uncomfortable administration of barium by enema after the cleansing procedure. Heretofore, no orally administered contrast agent has been available for visualization of the colon. The agents of the present invention, however, permit a full GI tract examination using an orally administered agent.

That variations from the preferred embodiments described above will be useful and will also be apparent to those skilled in the art. Therefore, the present invention is to be considered limited only by the appended claims.

I claim:

1. A process for visualization of the GI tract of a mammal comprising administering to the mammal a diagnostically effective amount of a contrast agent comprising an aqueous emulsion of an iodinated compound which iodinated compound is an aliphatic carboxylic acid of from 6-17 carbon atoms in the aliphatic chain exclusive of any branching in said aliphatic chain, said carboxylic acid being (a) iodinated directly or by incorporation therein of an iodinated substituent and (b) slightly soluble in water and which emulsion shows no visible evidence of separation into oil and water phases in the GI tract for at least about one hour as demonstrated by radiographic examination.

2. A process according to claim 1 wherein the carboxylic acid has an aromatic substituent to which the iodine is bound.

3. A process according to claim 2 wherein the iodinated compound is of the formula $(I)_n$ X—R—$CO_2H$ wherein X is an aromatic group, $_n$ is an integer of from 1-3 per aromatic nucleus and R is an aliphatic group of from 5 to 16 carbon atoms exclusive of branching.

4. A process according to claim 3 wherein the iodinated compound is iodoundecylenic acid.

5. A process for visualization of the GI tract of a mammal comprising administering to the mammal a diagnostically effective amount of a contrast agent comprising an aqueous emulsion of an iodinated compound convertible at least in part in the GI tract to an aliphatic carboxylic acid of from 6 to 17 carbon atoms in the aliphatic chain exclusive of any branching in the aliphatic chain, which compound is (a) iodinated directly in the aliphatic chain of the carboxylic acid or by incorporation therein of an iodinated substituent and (b) slightly soluble in water and which emulsion shows no visible evidence of separation into oil and water phases in the GI tract for at least about one hour as demonstrated by radiographic examination.

6. A process according to claim 5 wherein the aliphatic chain has an aromatic substituent to which the iodine is bound.

7. A process according to claim 6 wherein the iodinated compound is a compound convertible at least in part into a carboxylic acid of the formula $(I)_n$ X—R—$CO_2H$ wherein X is an aromatic group, $_n$ is an integer of from 1-3 per aromatic nucleus and R is an aliphatic group of from 5 to 16 carbon atoms exclusive of branching.

8. A process according to claim 5 wherein the iodinated compound convertible into the carboxylic acid is an ester, amide, anhydride or acid halide of the carboxylic acid.

9. A process according to claim 7 wherein the compound has the formula $(I)_n$ X—R—CO—R′ wherein X is an aromatic group, $_n$ is an integer of from 1-3 per aromatic nucleus, R is an aliphatic group of from 5-16 carbon atoms exclusive of branching and R′ is halogen or the residue of an alcohol, amine r carboxylic acid used to form an ester, amide or anhydride of the carboxylic acid.

10. A process according to claim 9 wherein the compound is iophendylate.

11. A process according to claims 1, 2, 3, 4, 5, 6, 7, 8, 9, or 10 wherein the contrast agent is comprised of up to about 45% by volume of the iodinated compound.

12. A process according to claim 11 wherein the contrast agent is administered orally.

13. A process according to claim 11 wherein the contrast agent is administered rectally.

* * * * *